United States Patent [19]

Allen et al.

[11] Patent Number: 4,935,604

[45] Date of Patent: Jun. 19, 1990

[54] METHOD AND APPARATUS FOR HOT AIR STERILIZATION OF MEDICAL INSTRUMENTS

[75] Inventors: Roy Allen, Southampton; Peter O. Sildve, Chalfont, both of Pa.

[73] Assignee: Dentronix, Inc., Ivyland, Pa.

[21] Appl. No.: 252,098

[22] Filed: Sep. 29, 1988

[51] Int. Cl.$^5$ .............................................. F27D 7/04
[52] U.S. Cl. .................................................. 219/400
[58] Field of Search ............... 219/400; 422/1, 2, 300, 422/307

[56] References Cited

U.S. PATENT DOCUMENTS

| | | |
|---|---|---|
| 857,240 | 6/1907 | Henning .............................. 422/300 |
| 976,001 | 11/1910 | Schmitt . |
| 1,419,031 | 6/1922 | Dufresne et al. . |
| 1,935,499 | 11/1933 | Boekel . |
| 2,015,775 | 10/1935 | Abraham . |
| 2,047,973 | 7/1936 | Lawton et al. . |
| 2,065,895 | 12/1936 | Jandat . |
| 2,093,334 | 9/1937 | Meitzler . |
| 2,126,168 | 8/1938 | Breuchaud . |
| 2,127,932 | 8/1938 | Pellkofer . |
| 2,209,099 | 7/1940 | Grueneklee ........................ 219/400 |
| 2,348,574 | 5/1944 | Ross . |
| 2,775,005 | 12/1956 | Weinberger . |
| 3,278,256 | 11/1966 | Skaller . |
| 3,351,422 | 11/1967 | Jones et al. . |
| 3,945,796 | 3/1976 | Nagamatsu et al. . |
| 4,229,415 | 11/1980 | Bryson . |
| 4,782,214 | 1/1988 | Voegtlin ............................. 219/400 |

FOREIGN PATENT DOCUMENTS

| | | |
|---|---|---|
| 172671 | 3/1952 | Austria . |
| 686059 | 1/1940 | Fed. Rep. of Germany . |
| 865937 | 8/1953 | Fed. Rep. of Germany . |
| 2411368 | 8/1979 | France .............................. 219/400 |
| 216859 | 1/1985 | German Democratic Rep. . |
| 438614 | 1/1975 | U.S.S.R. . |
| 909433 | 10/1962 | United Kingdom . |
| 1080202 | 8/1967 | United Kingdom ................ 219/400 |

Primary Examiner—Teresa J. Walberg
Attorney, Agent, or Firm—Panitch, Schwarze, Jacobs & Nadel

[57] ABSTRACT

A hot air sterilizer for medical instruments providing rapid sterilization cycle times includes a housing defining a sterilizing chamber. A fan is located in a heated air passage within the housing which extends around the sterilizing chamber from a bottom wall of the chamber to a top wall. The fan circulates air in a closed loop from the top to the bottom of the sterilizing chamber and through the passage. A heater is also located in the passage for heating the circulating air to a temperature sufficiently high for sterilization. Inlet and outlet cooling air passages, separate from the heated air passage, are provided extending through portions of the housing to the chamber. A separate fan, preferably in the inlet passage, circulates air through a portion of the housing along the inlet air passage and through the sterilizing chamber while bypassing the heated air passage and the heater and hot air circulating fan in that passage. Guide rails in the sterilizing chamber uniformly space removable racks each capable of supporting several hinged instruments and several other elongated instruments. The racks are self-supporting and may be removed for chairside use.

24 Claims, 4 Drawing Sheets

METHOD AND APPARATUS FOR HOT AIR STERILIZATION OF MEDICAL INSTRUMENTS

BACKGROUND OF THE INVENTION

1. Field of the Invention

The invention relates to hot air sterilization and, in particular, to self-contained hot air sterilizers with forced cooling to reduce sterilization cycle times.

2. Description of the Prior Art

Certain medical practices such as small dental and/or orthodontic practices require the availability of large numbers of instruments during a day in the treatment of many patients. In order to reduce the total number of instruments needed to support such practices, sterilization turn around times must be as short as possible. Accordingly, sterilizers with rapid cooling cycles are valuable to such individual practices.

Dry heat sterilization is increasingly becoming the method of choice for sterilizing medical instruments with carbide and carbon steel components. Such sterilization provides safety for all instruments which are chemically and moisture sensitive by introducing no foreign substances and by effectively eliminating moisture in the sterilizing atmosphere.

Medical dry heat sterilizers previously available for use in a practitioner's office typically have used the method of conductive heat transfer both to elevate the instrument loads to a sterilizing temperature and thereafter reduce the temperature of the instruments to a usable level.

Other approaches have been suggested. One suggested approach has been to provide forced air heating for sterilization but to make no provision for cooling. Another approach has been to provide forced air heating within a sterilizing chamber followed by forced air cooling of the outside of the sterilizing chamber walls. Still another suggested approach is the forced air heating and cooling of the contents of a sterilizing chamber by a single fan along a single air flow path through the sterilizing chamber.

One disadvantage suffered by all of these approaches with forced air cooling cycles is that cooling air is circulated through the sterilizer in such a way that it cools the sterilizing air heat source as well as the instruments and other objects being sterilized. In some approaches, cooling air is directed across the heat source before it is passed into the sterilizing chamber and therefore cools the heat source before cooling the contents of the chamber. In some approaches the cooling air must also cool the fan which had been used to circulate heated air through the sterilizing chamber. Cooling time for such sterilizers is extended by the time needed to additionally cool the heat source, and/or the hot air circulating fan.

SUMMARY OF THE INVENTION

The present invention is a hot air sterilizer for medical instruments comprising a housing and an enclosed sterilizing chamber defined within the housing. The sterilizer further comprises hot air circulating means for circulating heated air through the sterilizing chamber; cooling air passage means extending through a portion of the housing to the sterilizing chamber for conducting cooling air through the portion of the housing and the sterilizing chamber; and cooling air circulating means separate from the hot air circulating means and connected with the cooling air passage means for circulating cooling air from outside the housing through the portion of the housing and through the sterilizing chamber.

In yet another aspect, the invention is a hot air sterilizer for medical instruments comprising a housing; an enclosed sterilizing chamber defined within the housing; hot air passage means within the housing for removing air from one side of the sterilizing chamber and for introducing heated air into another side of the sterilizing chamber; heating means in the hot air passage means for heating air passing through the hot air passage means; and inlet cooling air passage means and outlet cooling air passage means separate from one another and from the hot air passage means for circulating cooling air through a portion of the housing and through the sterilizing chamber along paths bypassing the heater means.

In another aspect the invention is the method for hot air sterilizing medical instruments in a sterilizing chamber defined within a sterilizer housing comprising the steps of circulating air along a closed path within the housing substantially in one direction through the sterilizing chamber from one side of the sterilizing chamber to another side of the sterilizing chamber and through a hot air passage in the housing extending around the sterilizing chamber from the other side to the one side, heating the air in the hot air passage to a temperature sufficiently high for sterilization, and circulating cooling air through a portion of the housing and through the sterilizing chamber through cooling air passages bypassing the hot air passage.

Other important aspects of the invention include rack means adapted for receiving and supporting a plurality of hinged instruments in a generally vertical elongated orientation within the sterilizing chamber.

BRIEF DESCRIPTION OF THE DRAWINGS

The foregoing summary as well as the following detailed description of the preferred embodiment of the invention will be better understood when read in conjunction with the appended drawings, it being understood, however, that the invention is not limited to the precise arrangements illustrated. In the drawings.

DETAILED DESCRIPTION OF THE PREFERRED EMBODIMENTS

Referring now to the figures where like numerals are used to indicate like elements throughout, there is depicted in FIGS. 1-5 a presently preferred embodiment of a hot air sterilizer of the present invention, particularly adapted for sterilizing medical instruments, indicated generally at 10. The sterilizer 10 includes a housing 12, an insulated door 14 mounted to the housing by hinges 15 to cover the front side of the housing 12. The door provides access to an enclosed sterilizing chamber 16 defined within the housing 12 by first side wall 18 (left side in FIG. 1), back wall 20 (see FIG. 2), second side wall 22 (right side in FIG. 2), top wall 24 (see FIG. 2), bottom wall 26 and an inner wall 28 of the insulated door 14.

Figure 1:
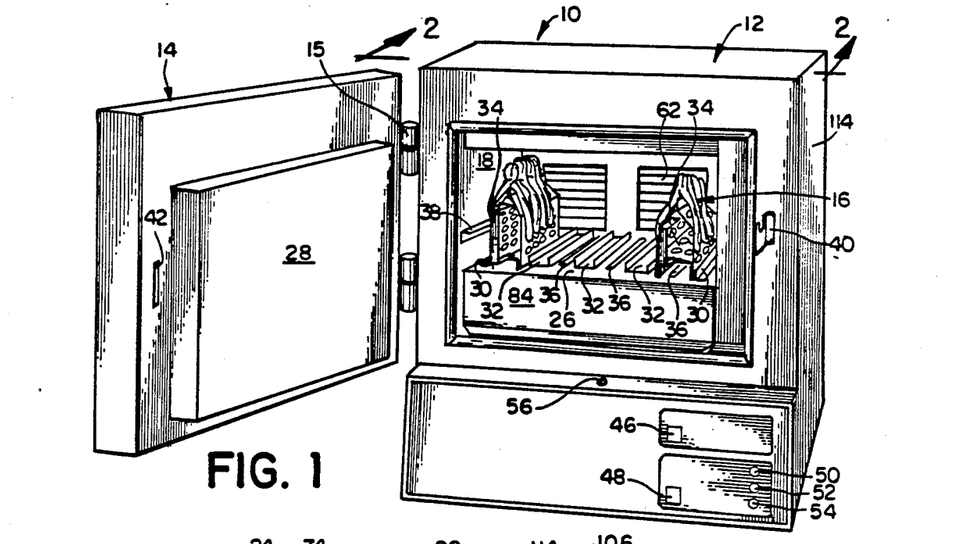
FIG. 1 is a diagrammatic, generally front isometric elevation of a preferred embodiment of a hot air sterilizer of the present invention with an open door.

Preferably, mounted to the bottom wall 26 of the sterilizing chamber are rack aligning means. Preferably, the rack aligning means are in the form of a pair of L-shaped end brackets 30 and a plurality of U-shaped brackets 32 intermediate the end brackets 30. The various brackets 30 and 32 are provided for aligning a plurality of upright instrument receiving racks, preferably four such racks, side-by-side in the chamber 16. Two of the preferred racks 34 are indicated in FIG. 1 and one is shown in greater detail in FIG. 6. The brackets 30 and 32 align each of the racks 34 directly over one of a plurality of openings 36, preferably elongated slots, provided through the bottom wall 26 of the sterilizing chamber 16. Preferably, a single slot 36 is provided for each instrument receiving rack 34. Slots 36 are the only air passage openings provided through the bottom wall 26.

Figure 2:
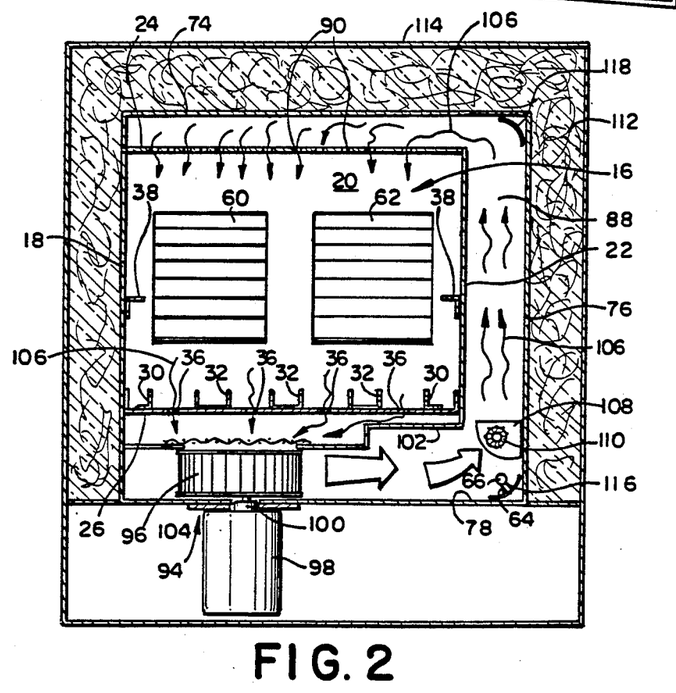
FIG. 2 is a diagrammatic vertical cross-sectional view of the sterilizer of FIG. 1 taken along the lines 2—2 of FIG. 1.

In addition to the illustrated upright instrument receiving racks 34, the sterilizer 10 is equipped to receive an apertured horizontal shelf (not depicted) extending across the width of the chamber 16 supported by an aligned pair of L-shaped brackets 38 on the first and second side walls 18 and 22 (see FIG. 2).

The upright portions of the L-shaped end brackets 30 and U-shaped intermediate brackets 32 define a set of guide rails for each of the instrument racks 34. The rails provide consistent, uniform spacing between the plurality of instrument receiving racks 34. This rack and rail loading system eliminates many variables in sterilizer loading, a common cause of ineffective sterilization, by assuring that the proper spacing and capacity requirements are always maintained.

Referring particularly to FIG. 1, a notched bracket 40 is mounted to and protrudes from the housing 12. Bracket 40 is received in a slot 42 on an inner side of the door 14 to assure alignment of the door 14. A rotatable handle (not depicted) on the front of the door rotates a latching bar engagable with the notch for latching the door 14 closed. A switch member 56 is exposed for contact with the door 14 when the door is closed. When closed, the door 14 depresses the member 56 which closes the contacts of a switch 58 (see FIG. 3) supplying power to the other electrical operating components of the sterilizer 10 as will be described.

The sterilizer 10 also includes operator controls and indicators, preferably at least a power on/off switch 46, a cycle start switch 48 and a plurality of indicator lights, preferably a heat-up indicator light 50, a sterilize indicator light 52 and a cycle complete light 54. The cycle start switch 48 is used to start a sterilization cycle. The heat-up light 50 indicates that the sterilizer 10 is in a heating-up cycle. The sterilize light 52 indicates when the sterilizer 10 is in a sterilizing (timed heat soak) cycle. The cycle complete light 54 comes on after a cooling cycle following the sterilize cycle has been completed.

Also visible in FIG. 1 are a cooling air inlet valve means in the form of a first set of inwardly opening louvers 60 and a cooling air outlet valve means in the form of a set of outwardly opening louvers 62. Each set of louvers 60, 62 is mounted to the back wall 20 of the sterilizing chamber 16.

Referring particularly now to FIG. 2, the details of a hot air sterilizing subsystem are depicted. The top wall 24, second (right) side wall 22 and bottom wall 26, of the sterilizing chamber 16, portions of the first (left) side wall 18 extending above and below the chamber 16, additional intermediate walls 74, 76 and 78, portions of the back wall 20 extending beyond the confines of the sterilizing chamber 16 to those walls 74, 76 and 78, and front walls 80, 82 and 84 (see FIG. 1) define an enclosed hot air passage means or duct indicated generally at 88 within the housing 12. The hot air passage duct 88 is provided in the housing 12 for removing air from one side of the sterilizing chamber 16 and for introducing heated air into another side of the sterilizing chamber 16. Preferably, the hot air passage duct 88 extends around the chamber 16 from one side, namely the bottom side, for drawing air from the chamber 16 through the plurality of slots 36 extending through the bottom wall 26 and preferably around the chamber 16 to another side, namely the opposing top side 24, for introducing the heated air into the chamber 16 through a plurality of openings 90 provided through the top wall 24. The openings 90 are distributed across the top wall 24 in a manner so as to provide uniform heating in the sterilizing chamber 16.

A hot air circulating means, indicated generally at 94, is provided for circulating heated air through the sterilizing chamber 16. The hot air circulating means 94 preferably includes a relatively medium speed, relatively low volume centrifugal (squirrel cage) type fan 96 positioned in the hot air passage duct 88 and an electric motor 98 driving the fan 96 through a shaft 100 extending through the intermediate wall 78. Positioned between the fan 96 and the bottom wall 26 of the sterilizing chamber 16 is another intermediate wall 102 having an opening 104 concentrically located over the center of the centrifugal fan 96. The opening 104 allows the fan 96 to draw air from the sterilizing chamber 16 through the plurality of elongated slots 36 in the direction indicated by arrows 106 extending through each of the slots 36. The fan 96 of the hot air circulating means 94 circulates air in a closed loop within the housing 12 in one direction through the hot air passage duct 88, as indicated by the arrows 106 within the passage duct 88 and through openings 90 in the top wall 24 and downward through the sterilizing chamber 16 from the top wall 24 to the bottom wall 26, and again through slots 36 and back into the hot air passage duct 88. The hot air circulating means 94 is also preferably located in the hot air passage duct 88 away from the sterilizing chamber 16 for cooling considerations to be described.

Figure 3:
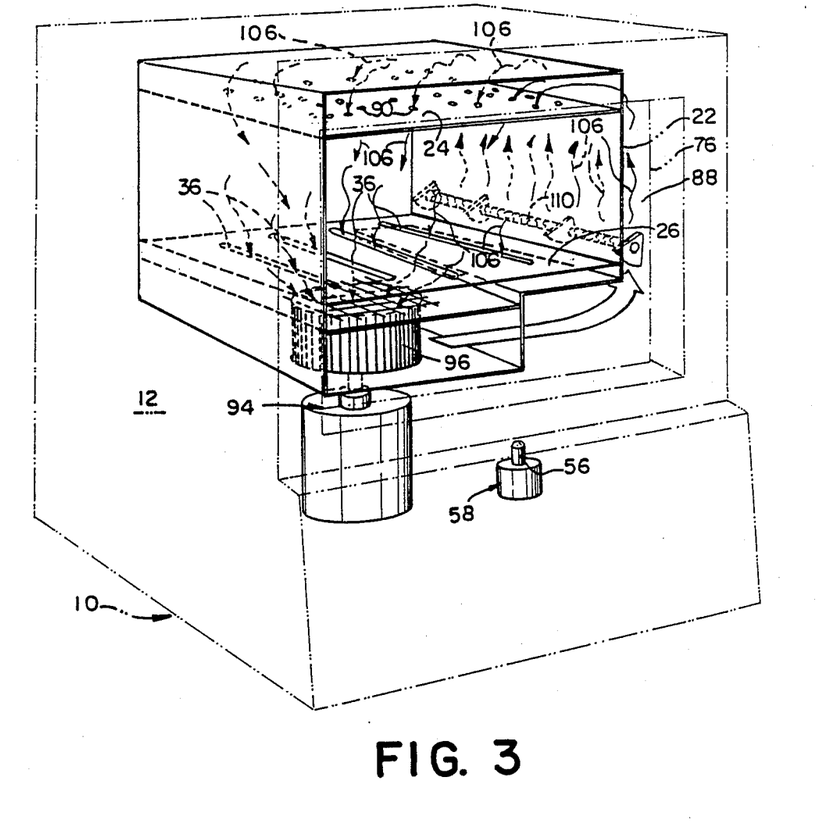
FIG. 3 is a diagrammatic, generally front isometric elevation of the sterilizer of FIGS. 1 and 2 with door removed and illustrated partially in phantom to expose the closed loop hot air circulation path and the components of the forced hot air sterilizing subsystem.
Figure 4:
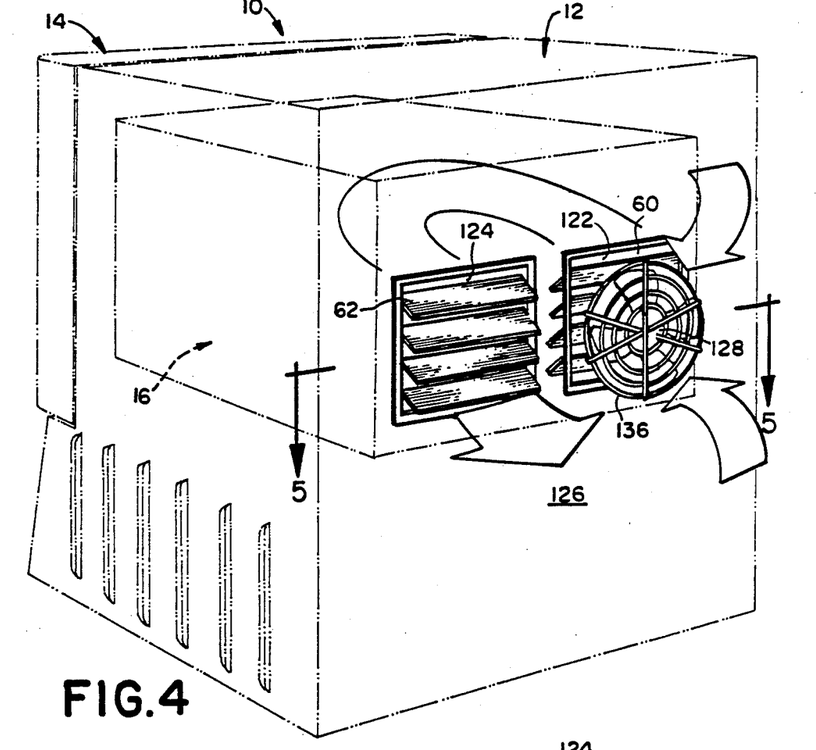
FIG. 4 is a diagrammatic, generally rear isometric elevation of the sterilizer of FIGS. 1-3 illustrated partially in phantom to expose the open loop cooling air circulation path and the components of the forced cooling air subsystem.

As is best seen in FIGS. 3 and 4, a plurality of insulated brackets 108 support heating means, preferably in the form of one or more electric resistance heater bars, one being indicated generally at 110. Preferably, the brackets 108 also provide the electrical connections to the bar 110. The heater bar 110 is preferably located within the hot air passage duct 88 and outside the sterilizing chamber 16 for heating the air in the hot air passage duct 88. The heater bar(s) 110 may be vertically oriented.

Referring back to FIG. 2, a bracket member 64 supports a temperature sensor 66 for a thermostatic switch 180 (shown in FIG. 7 and hereinafter discussed with respect to that figure) on a curved deflector plate 116.

The housing 12 is insulated by insulation 112 provided between exterior walls 114 of the housing 12 and interior walls including walls 18, 20, 74 and 76, surrounding the hot air passage duct 88 and the sterilizing chamber 16, for retaining heat generated during the sterilization cycle within the sterilizer 10. Though not required, curved deflector plates 116 and 118 can be provided in the lower and upper corners, respectively, of the vertical portion of the air passage duct 88 to assist in directing the air smoothly through those corners of the hot air passage duct 88. If curved plate 116 is omitted, other bracketry may be provided for supporting the temperature sensor 66.

Figure 5:
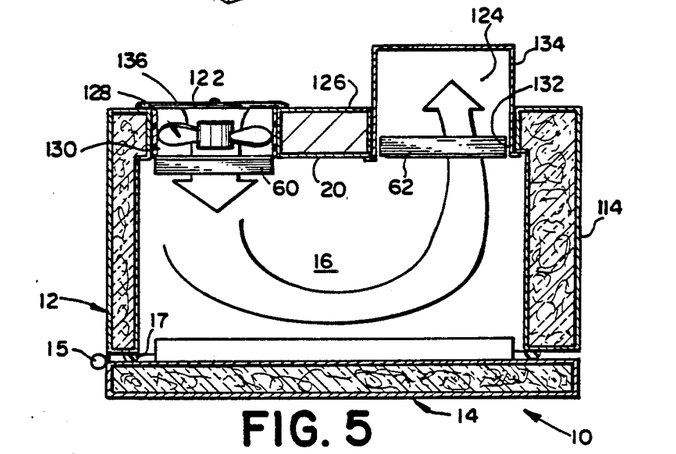
FIG. 5 is a diagrammatic, horizontal cross-sectional view of the sterilizer of FIGS. 1-4 taken along the lines 5—5 of FIG. 4.

FIGS. 4 and 5 illustrate the major elements of the sterilizer cooling subsystem and the open loop path of ambient, cooling air from outside the housing 12 through a portion of the housing 12 through the sterilizing chamber 16, indicated in phantom in FIG. 4 along an inlet cooling air passage 122 and an outlet cooling air passage 124. Each of the cooling air passages 122 and 124 extends through a back exterior wall 126 of the housing 14 and the back wall 20 of the sterilizing chamber 16.

A cooling air circulating means in the form of an electrically operated, relatively medium speed, relatively high volume axial type fan 128 is preferably mounted for rotation in a housing 130 which defines the inlet air cooling passage 122 extending between the back wall 126 of the housing 12 and the back wall 26 of the sterilizing chamber 16. A wire screen 136 is preferably provided on the back wall 126 of the housing 12 to cover the fan 128.

A duct 132 is formed between the back wall 126 of the housing 12 and back wall 20 of the sterilizing chamber 16 to define the outlet cooling air passage 124. Preferably, an air deflector 134 is attached to the rear of the housing at the outlet cooling air passage 124. Preferably, the deflector 134 has a set of mounting holes spaced so as to permit the deflector 134 to be selectively mounted to deflect the exhausting air either up or to the right side of the housing 12.

The sets of air pressure-operable louvers 60 and 62 (also see FIGS. 1 and 2) are mounted within the inlet cooling housing 130 and the outlet cooling duct 132 to form valves through which air may pass in only the proper direction inwardly through the inlet cooling air passage 122 and outwardly through the outlet cooling air passage 124. Thus, the louvers open the cooling air passages 122 and 124 during the cooling cycle and close those passages 122 and 124 at other times, particularly during the sterilization cycle, to prevent the loss of heated air. The inlet set of louvers 60 opens inwardly into the sterilizing chamber 16 under the pressure of air being circulated by the axial fan 128 through the inlet cooling air passage 122 into the sterilizing chamber 16. The outlet set of louvers 62 opens outwardly into the outlet cooling air passage 124 and opens when cooling air circulated by the axial fan through the inlet air passage 122 into the sterilizing chamber 16 builds up to a sufficiently high pressure within the sterilizing chamber 16.

The inlet set of louvers 60 and the outlet set of louvers 62 are not opened by heated air circulated through the sterilizing chamber 16 by the hot air centrifugal fan 96. This is because fan 96 merely circulates air through the hot air passage duct 88 and through the chamber 16 at a volume, rate and pressure sufficient to move the air, but insufficient to cause either the inlet or the outlet set of louvers 60 or 62 to open. The cooling air axial fan 128 is separate from the hot air centrifugal fan 96 and is mounted within the housing 12 outside the sterilizing chamber 16 and is, generally speaking, not significantly heated during the sterilization process. Consequently, the mass of the cooling air fan 128 need not be cooled during the cooling cycle, thereby shortening the cooling cycle. Similarly, each of the inlet and outlet cooling air passages 122 and 124 is separate from the hot air passage duct 88 so that the cooling air circulates through a portion of the housing 12 and through sterilizing chamber 16 along the cooling air passages 122 and 124 bypassing the hot air passage duct 88 and the electric heater 110 and heated air fan 96 contained therein so that cooling air is not diverted to cool those components. This reduces the time needed for cooling.

Figure 6:
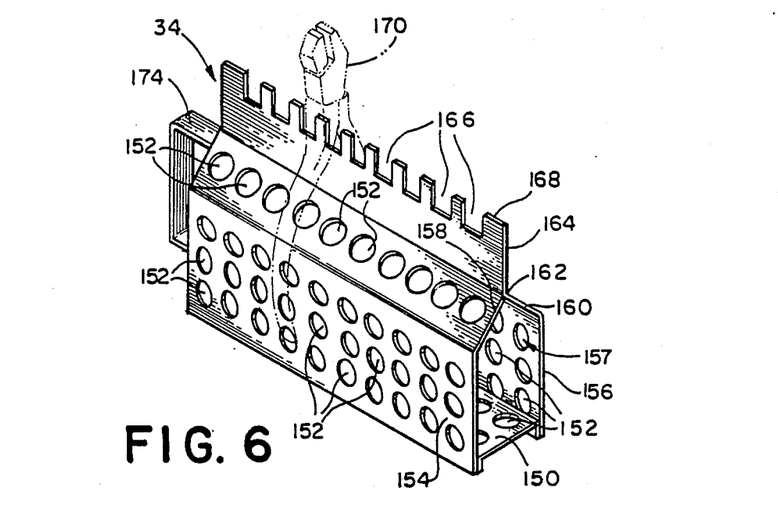
FIG. 6 is an diagrammatic, isometric view of a rack for use with the sterilizer of FIGS. 1-5.

FIG. 6 depicts in greater detail a preferred embodiment of a rack 34 for use with the hot air sterilizer 10. The rack 34 preferably includes a horizontal bottom wall 150 with perforations 152 and side walls 154 and 156 also with perforations 152. The side walls 154 and 156 extend slightly below the bottom wall 150 to form feet of the rack 34 and above the bottom wall 150 to form an instrument receiving cavity 157. At a predetermined distance above the bottom wall 150, upper portions 158 and 160 of side walls 154 and 156 are angled towards one another forming a peak 162. Preferably, each of the upper portions 158 and 160 includes perforations 152. Though the perforations 152 for the upper portion 160 are not seen in the figure, they are preferably substantially symmetric to the perforations 152 of the upper portion 158 which are visible in the figure. Preferably, the rack 34 is porous or open on all sides and is more porous or open than solid on all sides for good air flow therethrough from all directions.

A generally planar instrument support member 164 preferably is integrally formed with or attached to the peak 162 and extends vertically upwardly from the peak 162. The support member 164 preferably is provided with a plurality of cutouts 166 along a top edge 168 of the member 164. Each of the cutouts 166 is preferably sized to receive and support the hinged portion of a hinged medical instrument like pliers 170, indicated in phantom in the figure, with the handles of the instrument 170 draped over and further supported by the side walls 154 and 156. Preferably, the cutouts 166 are uniformly spaced from one another along the member 164 to provide uniform spacing of the hinged instruments 170 from one another along the rack 34 for uniform distribution of the heating load in the sterilizing chamber 16.

Other narrow, elongated instruments such as explorers, mirrors, scalers, etc. (not depicted) can be laid flat on the bottom wall 150 in the cavity 157 formed by the bottom wall 150 and the side walls 154 and 156 of the rack 34.

Preferably, a handle 174 is provided at one end of the rack 34 for ease of handling, particularly in loading and unloading the rack 34 from the sterilizer 10.

The perforated rack design, together with the guide rails defined by the L-shaped and U-shaped brackets 30 and 32, respectively, on the bottom wall 26 of the sterilizing chamber 16 (see FIG. 2) provide consistent spacing between the racks 34 and thus, the medical instruments within the sterilizer 10, assuring that the proper spacing and capacity requirement of the sterilizer are maintained. This eliminates many of the variables which are common causes of ineffective sterilization in other prior art hot air sterilizers. Preferably, heated air is directed from top to bottom of the sterilizer 10 and from outside the rack 34 to inside the rack 34 and through the elongated slots 36 in the bottom wall 26 of the sterilizing chamber 16. The rack 34 is designed to support a plurality of elongated hinged instruments in a generally vertically elongated orientation within the sterilizing chamber 16 so that hot air is drawn through as well as along the instruments. The rack 34 is freestanding, and can be removed from the sterilizer 10 and used to dispense instruments at chair side and then reloaded for another sterilization cycle.

Unhinged, oddly-shaped and oversize instruments may also be sterilized in the chamber 16 through the use of conventional flat, perforated racks (not depicted), supported across the width of the chamber 16 on the L-shaped brackets 38 attached to the side walls 18 and 22 of the sterilizing chamber 16. Racks may be marked with different indicia, for example, different colors, for segregating instruments or for identifying particular uses, locations (i.e. patient rooms, chairs), etc. for the instruments or the rack.

Figure 7:
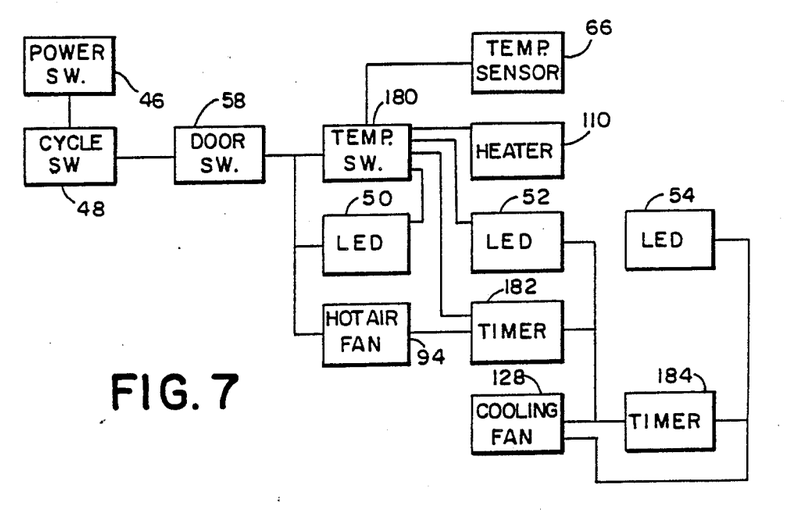
FIG. 7 is a block diagram illustrating the major components of the electrical control system with the other, major electrical components of the sterilizer.

FIG. 7 indicates in block diagram form the relation between the previously identified electrical components of the device and additional components constituting the major elements of a control means of the device 10.

The power on switch 46 is connected across the main electrical supply circuit (not depicted). The cycle switch 48 controls the supply of power from the main circuit to the other electrical components of the device 10. When both are closed, the cycle switch 48 and door switch 58 supply power to the first LED indicator light 50, the hot air circulating means 94 (for rotation of fan 96), and a temperature (thermostatic) switch 180. The temperature switch 180 in turn controls the supply of power to the heater means 110 and the temperature sensor means 66 which supplies a signal back to the temperature switch 180 for controlling the switching on and off of power to the heater means 110. The temperature switch 180 further controls the switching off of power to the first indicator LED 50 and to the supply of power to second indicator LED 52 and a timer 182. Timer 182 times the sterilizing (heat soak) cycle length and controls the switching off of power to the second indicator LED 52, the hot air circulating means 94, and the temperature switch 180. It further controls the switching on of power to the cool air circulating means fan 128 and to a second timer 184. The second timer 184 times the cool down cycle and controls the switching off of power to the cooling air fan 128 as well as the supplying of power to the third indicator LED 54 when the cooling cycle is complete. The cycle switch 48, door switch 58, temperature switch 180 and timers 182 and 184 preferably operate through a network of relays or other switching means (not depicted for clarity) well known to those skilled in the art for supplying power and switching off power to the other electrical components.

Operation of the device 10 is straightforward. The rack(s) 34 or other racks are loaded with instruments and/or other objects to be sterilized and loaded into the chamber 16. The door 14 is closed and the power on and cycle start switches 46 and 48 are actuated. Operation of the cycle start switch 48 causes the solenoid 58 to operate, locking door 14 during the heating cycle. The cycle start switch 48 also causes actuation of the heated air circulating means 94, operation of the heating means 110 and illumination of the first indicator light 50. The fan 96 of the hot air circulating means 94 circulates heated air within the housing 12 and sterilizing chamber 16 along a closed path, indicated in FIG. 2 by arrows 106, within the housing 12, substantially in one direction downward through the sterilizing chamber 16 from one side, namely the top side of the sterilizing chamber 16, to another side of the sterilizing chamber, namely, the opposing bottom side, and through the elongated slots 36 in the bottom wall 26 into hot air passage duct 88 which extends within the housing 12 around the sterilizing chamber 16 from the bottom side to the top side.

The heater 110 heats the air in the hot air passage duct 88 to a temperature sufficiently high to sterilize the objects in the chamber 16. Temperature is controlled through control of the operation of the heater 110 by means of the sensor 66 and the connected temperature switch 180. The heater 110 is operated by the switch 180 to reach and maintain a preferred operating temperature of at least about 375° F. in the chamber 16. When the preferred temperature is reached, the temperature switch 180 switches off power to the first indicator LED 50 and switches on power to the second indicator LED 52 indicating the warm-up cycle is complete and the sterilization heat soak cycle is on. Switch 180 also activates timer 182 which times the sterilization heat soak cycle. During the heat soak cycle, the switch 180 activates and deactivates the heater 110 to maintain temperature in the sterilizing chamber 16 within a predetermined range below the preferred operating temperature, for a time sufficient to sterilize the instruments or other objects being sterilized. The preferred sterilizing heat soak cycle is about 6 minutes.

When the first timer 182 times out, it deactivates the heater 110 and heated air circulating means (hot air fan) 94 and activates the cooling air circulating means fan 126. It further starts a second timer 184 controlling the length of time the cooling fan 126 operates to define a cooling cycle. That is the length of time is sufficient to cool an entire load of instruments to a safe use temperature and preferably is about ten minutes or less. Preferably, the complete sterilization cycle for the depicted sterilizer 10 is completed in about 20 minutes, including cool down. When the second timer 184 times out, it switches off the cooling air fan 128, switches on the third indicator LED 54 indicating completion of an entire sterilization and cooling cycle. The racks 34 may then be unloaded from the sterilizing chamber 16 for use.

The present invention may be embodied in other specific forms without departing from the spirit or central attributes thereof. Accordingly, reference should be made to the appended claims, rather than to the foregoing specifications, as indicating the scope of the invention.

We claim:

1. A hot air sterilizer for medical instruments comprising:
   a housing;
   an enclosed sterilizing chamber defined within the housing;

hot air circulating means for circulating heated air through the sterilizing chamber;

cooling air passage means extending from the sterilizing chamber through a portion of the housing to the ambient atmosphere outside the housing and the sterilizer for conducting cooling air from outside the sterilizer through the portion of the housing and the sterilizing chamber; and cooling air circulating means separate from the hot air circulating means and connected with the cooling air passage means for circulating ambient cooling air from outside the housing and the sterilizer through the portion of the housing and through the sterilizing chamber.

2. The sterilizer of claim 1 further comprising hot air passage means within the housing for removing air from one side of the sterilizing chamber and for introducing heated air into another side of the sterilizing chamber.

3. The sterilizer of claim 2 wherein the one side and the other side are opposing sides of the sterilizing chamber.

4. The sterilizer of claim 3 wherein the sterilizing chamber has opposing top and bottom walls, wherein the one side is the bottom wall and the other side is the top wall, wherein the hot air passage means extends around the sterilizing chamber from the bottom wall to the top wall and wherein the hot air circulating means circulates air in one direction through the hot air passage means and through the sterilizing chamber from the top wall to the bottom wall.

5. The sterilizer of claim 4 further comprising heating means in the hot air passage means within the housing and outside the sterilizing chamber for heating air in the hot air passage means.

6. The sterilizer of claim 5 further comprising control means for deactivating the heating means and the hot air circulating means and for activating the cooling air circulating means when a sterilization cycle has been completed.

7. A hot air sterilizer for medical instruments comprising:

a housing;

an enclosed sterilizing chamber defined within the housing;

hot air circulating means for circulating heated air through the sterilizing chamber, the sterilizing chamber including a bottom wall having a plurality of openings permitting air to be circulated by the hot air circulating means through the bottom wall; and rack aligning means within the sterilizing chamber for aligning a plurality of instrument receiving racks side by side in the sterilizing chamber with each of the racks aligned directly over and opening.

8. The sterilizer of claim 7 further comprising rack means within the sterilizing chamber, the rack means being adapted for receiving and supporting a plurality of hinged instruments in a generally vertically elongated orientation within the chamber.

9. A hot air sterilizer for medical instruments comprising:

a housing;

an enclosed sterilizing chamber defined within the housing;

hot air passage means within the housing for removing air from one side of the sterilizing chamber and for introducing heated air into another side of the sterilizing chamber;

heating means in the hot air passage means for heating air passing through the hot air passage means; and inlet cooling air passage means and outlet cooling air passage means separate from one another and from the hot air passage means for circulating cooling air through a portion of the housing and through the sterilizing chamber along paths bypassing the heating means, at least one of the inlet and outlet cooling air passage means extending from the sterilizing chamber through the housing to ambient atmosphere outside the housing and the sterilizer.

10. The sterilizer of claim 9 wherein the sterilizing chamber has opposing top and bottom walls, wherein the hot air passage means extends around the sterilizing chamber from the bottom wall to the top wall and further comprising hot air circulating means for circulating air in one direction through the sterilizing chamber from the top wall to the bottom wall and through the hot air passage means.

11. The sterilizer of claim 10 wherein the hot air circulating means is located in the hot air passage means.

12. The sterilizer of claim 9 further comprising:

hot air circulating means in the hot air passage means for circulating air past the heating means and through the hot air passage means into the sterilizing chamber; and cooling air circulating means separate from the hot air circulating means, the cooling air circulating means being connected with only one of the inlet and outlet cooling air passage means for circulating air from outside the housing through the portion of the housing and through the sterilizing chamber along the inlet and outlet cooling air passage means.

13. The sterilizer of claim 12 further comprising inlet valve means connected with the inlet cooling air passage means and outlet valve means connected with the outlet cooling air passage means for opening and closing the respective cooling air passage means.

14. The sterilizer of claim 13 wherein at least one of the inlet and outlet valve means comprises an air pressure operable louver.

15. A method for hot air sterilization of medical instruments in a sterilizing chamber defined within a sterilizer housing comprising the steps of:

circulating air along a closed path within the housing substantially in one direction through the sterilizing chamber from one side of the sterilizing chamber to another side of the sterilizing chamber and through a hot air passage in the housing extending around the sterilizing chamber from the other side to the one side;

heating the air in the hot air passage to a temperature sufficiently high for sterilization; and circulating cooling air from outside the housing through a portion of the housing and through the sterilizing chamber along cooling air passages bypassing the hot air passage.

16. The method of claim 15 wherein the step of circulating cooling air comprises blowing ambient air from outside the housing and the sterilizer through the cooling passage into the sterilizing chamber to pressurize the sterilizing chamber.

17. A hot air sterilizer for medical instruments comprising:
a housing;
an enclosed sterilizing chamber defined within the housing;
hot air circulating means for circulating heated air through the sterilizing chamber;
cooling air passage means extending through a portion of the housing to the sterilizing chamber for conducting cooling air through the portion of the housing and the sterilizing chamber;
cooling air circulating means separate from the hot air circulating means and connected with the cooling air passage means for circulating cooling air from outside the sterilizing chamber through the portion of the housing and through the sterilizing chamber; and
valve means connected with the cooling air passage means for opening and closing the cooling air passage means, the valve means being operable by air circulated by the cooling air circulating means.

18. The sterilizer of claim 17 wherein the valve means comprises an air pressure operable louver.

19. The sterilizer of claim 17 further comprising:
another cooling air passage through the housing and into the sterilizing chamber, the other cooling air passage means being separate from the hot air passage means; and
another valve means connected with the other cooling air passage means for opening and closing the other cooling air passage means, the other valve means being operable by air circulated by the cooling air circulating means.

20. A hot air sterilizer for medical instruments comprising:
a housing;
an enclosed sterilizing chamber defined within the housing and having a bottom wall and a plurality of openings through the bottom wall;
hot air passage means within the housing for removing air from the sterilizing chamber through the plurality of openings in the bottom wall and for introducing heated air into the sterilizing chamber through a wall of the sterilizing chamber other than the bottom wall;
heating means in the hot air passage means for heating air passing through the hot air passage means;
hot air circulating means for circulating heated air from the hot air passage means through the sterilizing chamber and through the plurality of openings in the bottom wall back into the hot air passage means;
cooling air passage means for conducting cooling air through a portion of the housing and through the sterilizing chamber; and
rack aligning means within the sterilizing chamber for aligning a plurality of instrument receiving racks side-by-side in the sterilizing chamber with each of the racks being aligned over an opening in the bottom wall.

21. The sterilizer of claim 20 further comprising rack means within the sterilizing chamber, the rack means being adapted for receiving and supporting a plurality of hinged instruments in a generally vertically elongated orientation within the sterilizing chamber.

22. The sterilizer of claim 21 wherein the rack means is removable from the housing and further comprises handle means for grasping the rack.

23. The sterilizer of claim 22 wherein the rack means has openings on all sides for circulating air from any direction through the rack means.

24. The sterilizer of claim 20 wherein the hot air passage means extends around the sterilizing chamber from the bottom wall to a top wall of the sterilizing chamber and wherein heated air from the hot air passage means is introduced into the sterilizing chamber through openings in the top wall whereby the heated air is circulated through the sterilizing chamber from the top wall to the bottom wall.

* * * * *